US012690919B2

(12) United States Patent
Wu et al.

(10) Patent No.: US 12,690,919 B2
(45) Date of Patent: Jul. 28, 2026

(54) LASER ABLATION CATHETER

(71) Applicant: Micro Energy Medical Technology Co., Ltd, Shenzhen (CN)

(72) Inventors: Nan Wu, Shenzhen (CN); Shufen Pan, Shenzhen (CN)

(73) Assignee: Micro Energy Medical Technology Co., Ltd, Shenzhen (CN)

( * ) Notice: Subject to any disclaimer, the term of this patent is extended or adjusted under 35 U.S.C. 154(b) by 362 days.

(21) Appl. No.: 18/195,165

(22) Filed: May 9, 2023

(65) Prior Publication Data

US 2023/0363818 A1      Nov. 16, 2023

(30) Foreign Application Priority Data

May 12, 2022    (CN) .......................... 202210512450.3

(51) Int. Cl.
| | |
|---|---|
| *A61B 18/20* | (2006.01) |
| *A61B 18/22* | (2006.01) |
| *A61B 18/24* | (2006.01) |
| *A61B 18/00* | (2006.01) |

(52) U.S. Cl.
CPC .............. *A61B 18/24* (2013.01); *A61B 18/22* (2013.01); *A61B 2018/00577* (2013.01)

(58) Field of Classification Search
CPC ............................................... A61B 18/22–26
See application file for complete search history.

(56) References Cited

U.S. PATENT DOCUMENTS 5,324,285 A * 6/1994 Cannon ................ A61B 18/245
                                                                606/15
2025/0017452 A1* 1/2025 Giuliani ................. A61B 1/273

FOREIGN PATENT DOCUMENTS

WO    WO-2022073922 A1 *  4/2022    ......... A61B 18/1492
WO    WO-2023099582 A1 *  6/2023    ............. A61B 18/22

* cited by examiner

*Primary Examiner* — Lynsey C Eiseman
(74) *Attorney, Agent, or Firm* — Inskeep IP Group, Inc.

(57)        ABSTRACT

Provided is a laser ablation catheter, including a laser optical fiber bundle, an adjustable head, an outer tube, an overtube and a connector. The outer tube wraps the laser fiber bundle. The adjustable head includes an adjustable stent, the adjustable stent is made of a shape memory material and is sleeved outside one end of the outer tube. The connector is connected to the other end of the outer tube, and the laser fiber bundle can be connected to a laser generator through the connector. The overtube is sleeved outside the adjustable stent for compressing the adjustable stent. At least one end of the adjustable stent is a movable end, and the movable end is slidingly connected to the outer tube. When the overtube is withdrawn, the movable end can provide conditions for the deformation of the adjustable stent.

8 Claims, 3 Drawing Sheets

21

21

LASER ABLATION CATHETER

CROSS-REFERENCE TO RELATED APPLICATION

This patent application claims the benefit and priority of Chinese Patent Application No. 2022105124503, filed with the China National Intellectual Property Administration on May 12, 2022, the disclosure of which is incorporated by reference herein in its entirety as part of the present application.

TECHNICAL FIELD

The present disclosure relates to the technical field of laser ablation catheters, in particular to a laser ablation catheter.

BACKGROUND

Coronary heart disease (CHD) is a disease with a high morbidity and mortality rate. Percutaneous coronary intervention (PCI) is one of the most important surgical methods at present.

Chronic total occlusion (CTO) of coronary artery in PCI is always a difficult point in coronary intervention. The process of CTO formation is the evolution process of thrombosis with progressive fibrosis and calcification on the basis of severe coronary stenosis or acute coronary occlusion. The blood flow shear stress at the proximal end (near the surgical operator's end) and the distal end (far away from the surgical operator's end) of CTO occlusion segment is different. The proximal fibrous cap is formed by fibrous tissue surrounding thrombus and lipid composition, which is hard due to high fibrous tissue components caused by large blood flow impact and the high fibrous tissue components. According to the calcification degree of plaques, the plaques can be divided into soft plaques, hard plaques and mixed plaques. The calcification degree of plaques may affect the difficulty of the advancement of guide wires. The more serious the calcification, the more difficult it is for the guide wire to enter the tissue space.

Excimer laser coronary atherectomy (ELCA) is a relatively new PCI treatment. Excimer laser is a cold light source for ablating plaques through laser catheter. Because of its short wavelength and shallow ablation depth, ELCA has obvious clinical effect and low complication rate, so it has become the choice of interventional therapy for complex coronary lesions. Clinical studies have proved that ELCA is a safe, feasible and effective collaborative tool for treating CTO lesions.

For lesions where the guide wires can pass but other interventional instruments such as balloons cannot pass or expand, plaques can be ablated by laser to open up a pathway. However, for lesions where the guide wire cannot pass, laser ablation has a high risk of vessel perforation, ELCA is not recommended in this case. At present, there is no ideal PCI treatment method and device for CTO lesions where the guide wire cannot pass.

SUMMARY

For the shortcomings in the prior art, it is provided a laser ablation catheter according to an embodiment of the present disclosure, which can overcome the defect that the existing laser ablation catheter is easy to damage a target vessel during CTO procedure.

The laser ablation catheter includes:

a laser fiber bundle, an adjustable head, an outer tube, an overtube, and a connector.

The outer tube wraps the laser fiber bundle. The adjustable head includes an adjustable stent, the adjustable stent is made of a shape memory material and is sleeved outside one end of the outer tube. The connector is connected to the other end of the outer tube, and the laser fiber bundle can be connected to a laser generator through the connector.

The overtube is sleeved outside the adjustable stent for compressing the adjustable stent.

At least one end of the adjustable stent is a movable end, and the movable end is slidingly connected to the outer tube. When the overtube is withdrawn, the movable end can provide conditions for the deformation of the adjustable stent.

As a further alternative solution of the laser ablation catheter, one end of the adjustable stent is a movable end, the other end of the adjustable stent is a fixed end, and the fixed end is fixedly connected to the outer tube.

As a further alternative solution of the laser ablation catheter, one end, away from the connector, of the adjustable stent is the movable end, and the end, close to the connector, of the adjustable stent is the fixed end.

As a further alternative solution of the laser ablation catheter, the tail end of the outer tube is provided with a limiting stage for preventing the movable end from sliding out of the outer tube.

As a further alternative solution of the laser ablation catheter, one end, away from the connector, of the adjustable stent is the fixed end, and the other end of the adjustable stent is the movable end.

As a further alternative solution of the laser ablation catheter, the adjustable head further includes an annular structure, and the annular structure is fixedly connected to both ends of the adjustable stent.

As a further alternative solution of the laser ablation catheter, the adjustable stent is made of nickel-titanium alloy.

As a further alternative solution of the laser ablation catheter, the adjustable stent is composed of nickel-titanium alloy wires by a weaving process.

As a further alternative solution of the laser ablation catheter, the adjustable stent is composed of nickel-titanium alloy sheets by a sheet metal process.

As a further alternative solution of the laser ablation catheter, the adjustable stent is made by a laser cutting process.

The implementation of the embodiment of the present disclosure has the following beneficial effects:

An adjustable head is added at the head end of the laser ablation catheter, which can adapt to the dimension of the target vessel after reaching the lesion location of the target vessel, thereby keeping the laser ablation catheter at the center of the vessel. Therefore, the laser can be concentrated in the lesion location to the greatest extent to reduce the adverse effects on the vessel wall of the target vessel while maximizing the laser ablation effect, and then the risk of complications of the vessel wall is reduced, and the success rate of surgery is improved.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

In the drawings.

Figure 1:
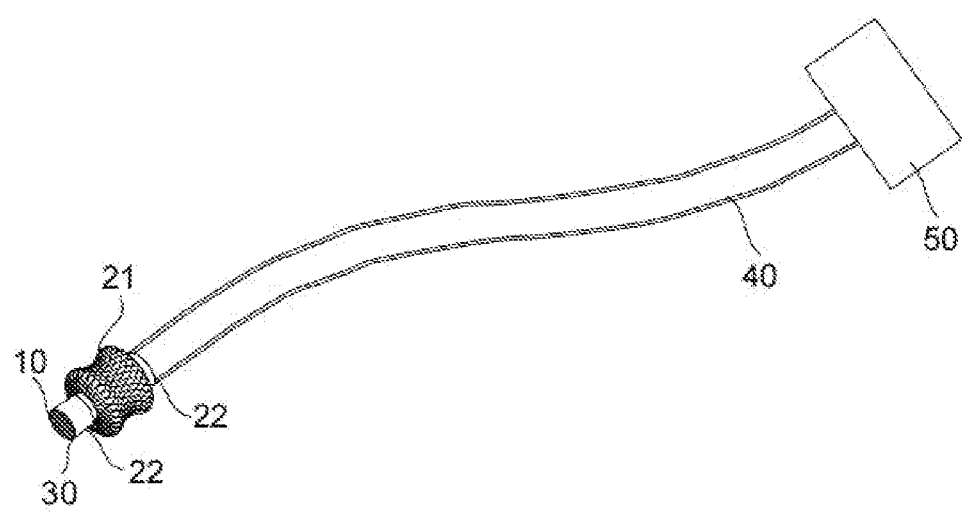
FIG. 1 is a structure schematic diagram of a laser ablation catheter in accordance with an embodiment of the present disclosure.

The meanings of the reference numerals are as follows: 10—laser fiber bundle; 21—adjustable stent; 22—annular structure; 30—outer tube; 31—limiting stage; 40—overtube; 50—connector.

DETAILED DESCRIPTION OF THE EMBODIMENTS

For ease of understanding of the present disclosure, the present disclosure is described more fully below with reference to the accompanying drawings. Preferred embodiments of the present disclosure are set forth in the accompanying drawings. The present disclosure may, however, be embodied in many different forms and is not limited to the embodiments described herein. Rather, these embodiments are provided for the purpose of providing a more thorough and thorough understanding of the present disclosure.

It should be noted that when an element is referred to as being "fixed to" another element, it may be directly on the other element or intervening elements may also be present. When an element is considered to be "connected" to another element, it may be directly connected to another element or intervening elements may be present at the same time. As used herein, the terms "vertical", "horizontal", "left", "right" and the like are merely intended for purpose of illustration.

Unless defined otherwise, all technical and scientific terms used herein have the same meaning as commonly understood by one of ordinary skill in the art. The terminology used herein is for the purpose of describing specific embodiments only and is not intended to limit the present disclosure. The term "and/or" as used in the present disclosure includes any and all combinations of one or more related listed items.

It is provided a laser ablation catheter according to an embodiment of the present disclosure, which can overcome the defect that the existing laser ablation catheter is easy to damage the target vessel during CTO procedure.

Figure 2:
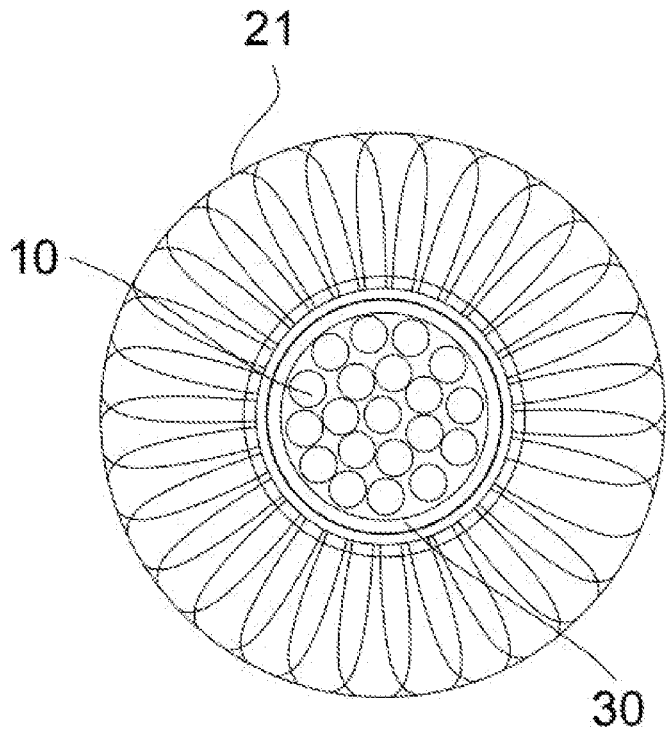
FIG. 2 is a structure schematic diagram of the cross section of a laser ablation catheter in accordance with an embodiment of the present disclosure.

With reference to FIG. 1 to FIG. 2, a structure of the laser ablation catheter includes a laser fiber bundle 10, an adjustable head, an outer tube 30, an overtube 40, and a connector 50. The outer tube 30 wraps the outside of the laser fiber bundle 10, the adjustable head includes an adjustable stent 21, and the adjustable stent 21 is made of a shape memory material and is sleeved outside one end of the outer tube 30. The connector 50 is connected to the other end of the outer tube 30, and the laser fiber bundle 10 can be connected to a laser generator through the connector 50, thus emitting laser to irradiate the lesion location of a target vessel to ablate the lesion. The overtube 40 is sleeved outside the adjustable stent 21 for compressing the adjustable stent 21. At least one end of the adjustable stent 21 is a movable end, and the movable end is slidingly connected to the outer tube 30. When the overtube 40 is withdrawn, the movable end can provide conditions for the deformation of the adjustable stent 21.

The working process of the laser ablation catheter is as follows: initially, the adjustable stent 21 is compressed in the overtube 40; after the laser ablation catheter extends into the lesion location of the target vessel, the overtube 40 is withdrawn, and the adjustable stent 21 expands to abut against the inner wall of the target vessel, thus fixing the laser ablation catheter in the middle of the target vessel, and ensuring that the laser emitted from the laser fiber bundle 10 can accurately irradiate the lesion location. During expansion and deformation, the radial dimension of the adjustable stent 21 is increased while the axial dimension is decreased, and thus the movable end is provided to ensure the smooth expansion of the adjustable stent 21.

The adjustable head is added at one end of the laser ablation catheter, which can adapt to the dimension of the target vessel after reaching the lesion location of the target vessel, thus keeping the laser ablation catheter at the center of the target vessel. Therefore, the laser can be concentrated in the lesion location to the greatest extent to reduce the adverse effects on the vessel wall of the target vessel while maximizing the laser ablation effect, and then the risk of complications of the vessel wall is reduced, and the success rate of surgery is improved.

In an embodiment, the maximum profile diameter of the adjustable stent 21 is from 0.6 mm to 4 mm.

In an embodiment, the adjustable head further includes an annular structure 22. The annular structure 22 is fixedly connected to both ends of the adjustable stent 21 for ensuring structural stability of the adjustable stent 21. In the absence of the annular structure 22, fixed connection points are required to exist between constituent components of the adjustable stent 21 (e.g., metal wires, metal strips or some polymers) to ensure the structural integrity of the adjustable stent; however, the existence of these connection points may weaken the deformation ability of the adjustable stent 21 to a certain extent and increase the processing difficulty. By introducing the annular structure 22, the tail ends of the constituent components of the adjustable stent 21 can be directly fixed to the annular structure 22, and the fixed connection points between the constituent components can be reduced or even cancelled, thus reducing the processing difficulty of the adjustable stent 21 and improving the deformation ability of the adjustable stent 21.

In a specific embodiment, the annular structure 22 is made of a metallic material.

In another specific embodiment, the annular structure 22 is fixedly connected to the outer tube 30 by thermal splicing or glue bonding.

In an embodiment, one end of the adjustable stent 21 is a movable end, the other end of the adjustable stent 21 is a fixed end, and the fixed end is fixedly connected to the outer tube 30.

In a specific embodiment, one end, away from the connector 50, of the adjustable stent 21 is the movable end, and the other end of the adjustable stent 21 is the fixed end.

In certain surgical procedures, a situation that the vessel wall changes from large to small may occur, and the vessel wall may squeeze the adjustable stent 21 at the moment, leading to the reduction of the radial dimension and the increase of the axial dimension of the adjustable stent 21, and pushing the movable end to move towards the tail end of the outer tube 30, and thus the movable end may slip off the outer tube 30.

To avoid such a situation, there are two options available.

In a more specific embodiment, sufficient distance is reserved between the movable end and the tail end of the outer tube 30 to ensure that the movable end is still kept on the outer tube 30 when the adjustable stent 21 is squeezed to press against the surface of the outer surface 30 due to small vessel dimension.

In this solution, as the sufficient distance is required to be reserved between the movable end and the tail end of the outer tube 30, the supporting effect of the adjustable stent 21 on the tail end of the laser ablation catheter is relatively poor, i.e., there may be a problem that the laser does not irradiate the center of the lesion in a concentrated manner; and the supporting effect may be lost when the adjustable stent 21 is pressed against the surface of the outer tube 31. The advantage of this solution is that the structure is simple and the production is convenient.

Figure 3:
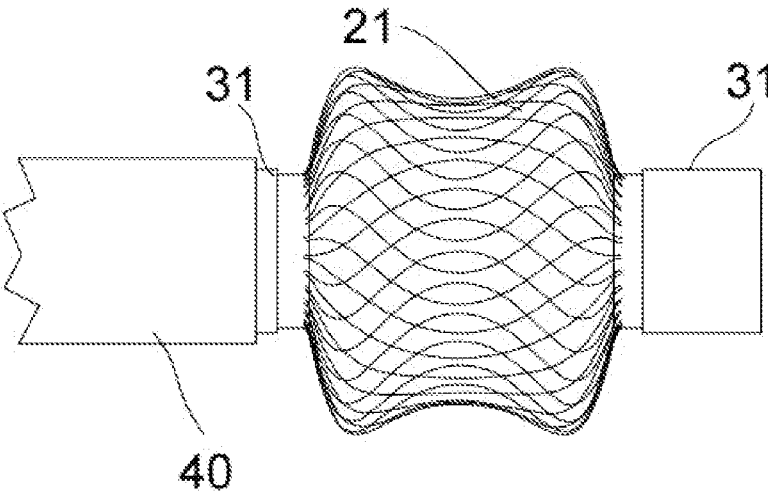
FIG. 3 is a structure schematic diagram of an adjustable head end of a laser ablation catheter in accordance with an embodiment of the present disclosure.

In another more specific embodiment, referring to FIG. 3, the outer tube 30 is provided with a limiting stage 31 at the position close to the movable end, the limiting stage 31 has a radial dimension greater than that of the movable end, thereby preventing the movable end from slipping out of the outer tube 30.

In a further specific embodiment, relative positions of the limiting stage 31 and the outer tube 30 are adjustable, that is, the moving range of the movable end of the adjustable stent 21 can be limited by adjusting the position of the limiting stage 31, thereby further limiting the radial dimension change range of the adjustable stent 21, and making the adjustable stent 21 better adapt to surgeries under different vessel dimension conditions.

In a still further specific embodiment, the outer tube 30 is provided with multiple clamping grooves, and the limiting stage 31 is clamped with the outer tube 30, and the position of the limiting stage 31 can be adjusted by selecting different clamping grooves.

The advantage of the solution employing the limiting stage 31 is that the radial dimension of the adjustable stent 21 can be better controlled.

In another specific embodiment, one end, away from the connector 50, of the adjustable stent 21 is the fixed end, and the other end of the adjustable stent 21 is the movable end.

With such a structure, in the process of withdrawing the laser ablation catheter after the surgery, the friction between the vessel wall and the adjustable stent 21 may make the movable end tend to retract relative to a withdrawal direction, which may make the radial dimension of the adjustable stent 21 tend to increase, thus enabling the adjustable stent 21 to play a role in supporting the vessel wall better during the withdrawing, and facilitating the withdrawal of the laser ablation catheter. Moreover, such a structure does not require an additional limiting stage 31 on the outer tube 30, and the processing process is simpler. Therefore, such a structure is a preferred solution in practice.

In order to prevent the foregoing situation that the adjustable stent 21 is squeezed to press against the outer tube 30 due to small vessel dimension, in a more specific embodiment, the outer tube 30 is provided with a limiting stage 31 at the position close to the movable end, thereby limiting the deformation range of the adjustable stent 21.

In yet another specific embodiment, the fixed end is fixedly connected to the outer tube 30 by a thermal splicing or glue bonding process.

In another embodiment, please continuing to refer to FIG. 3, both ends of the adjustable stent 21 are movable ends. With such a structure, the relative positions of the adjustable stent 21 and the outer tube 30 are difficult to fix, and the outer tube 30 are required to be provided with limiting stages 31 at the positions close to the two movable ends of the adjustable stent 21, thus preventing the adjustable stent 21 from sliding freely on the outer tube 30.

It should be appreciated that the adjustable stent 21 may be made in a variety of production processes, of which only some preferred solutions are described below.

In an embodiment, the adjustable stent 21 is made of nickel-titanium alloy.

The advantage of using the nickel-titanium alloy is that the nickel-titanium alloy belongs to one of shape memory metals, which can be recovered to its original shape under the temperature environment of blood and has good corrosion resistance, and thus has been used in medical field maturely.

Figure 4:
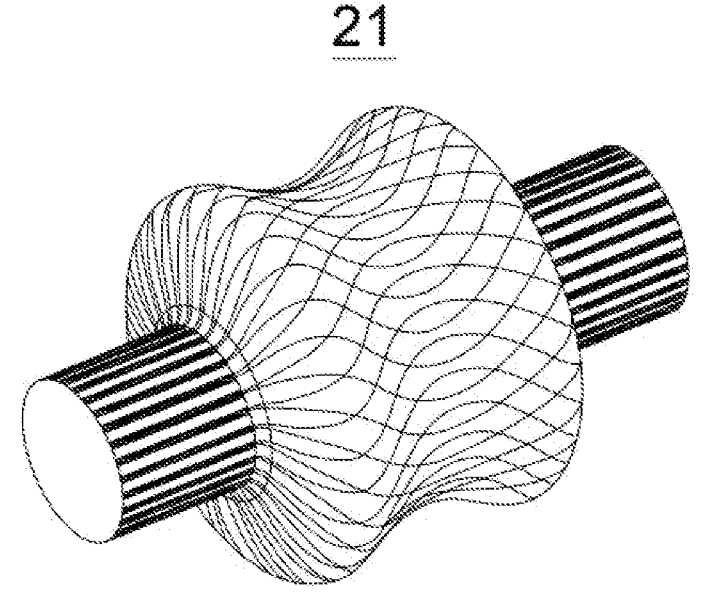
FIG. 4 is a structure schematic diagram of an adjustable stent made by a weaving process in accordance with an embodiment of the present disclosure.

In a specific embodiment, referring to FIG. 4, the adjustable stent 21 is composed of nickel-titanium alloy wires by a weaving process.

In a more specific embodiment, the adjustable stent 21 is made by weaving nickel-titanium alloy wires having diameters of 0.05 mm to 0.1 mm into woven tubes of 2 mm to 3 mm, fixing the woven tubes into a designed contour by a setting die, in which the maximum diameter of the contour is from 1.5 mm to 3 mm, and finally, putting the shaped woven mesh into a vacuum heat treatment furnace for heat-setting treatment. It may be understood that these numbers are only empirical values in practice and are not to be construed as limiting the present disclosure.

In another specific embodiment, the adjustable stent 21 is composed of nickel-titanium alloy sheets by a sheet metal process.

Figure 5:
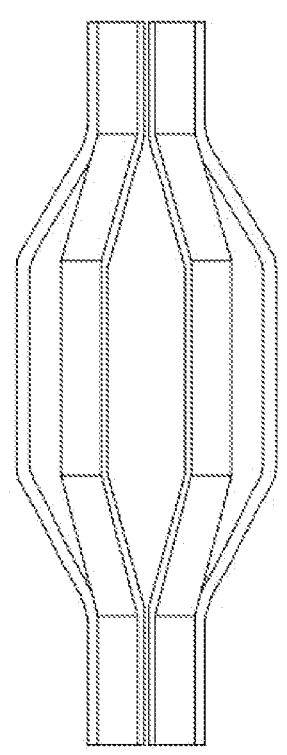
FIG. 5 is a structure schematic diagram of an adjustable stent made by a sheet metal process in accordance with an embodiment of the present disclosure.

In a more specific embodiment, referring to FIG. 5, the adjustable stent 21 is composed of multiple nickel-titanium alloy sheets surrounding the outer tube 30, the middle of which is protruded to support the vessel wall, and the ends of which are folded into rounded openings for connection with the outer tube 30.

Figure 6:
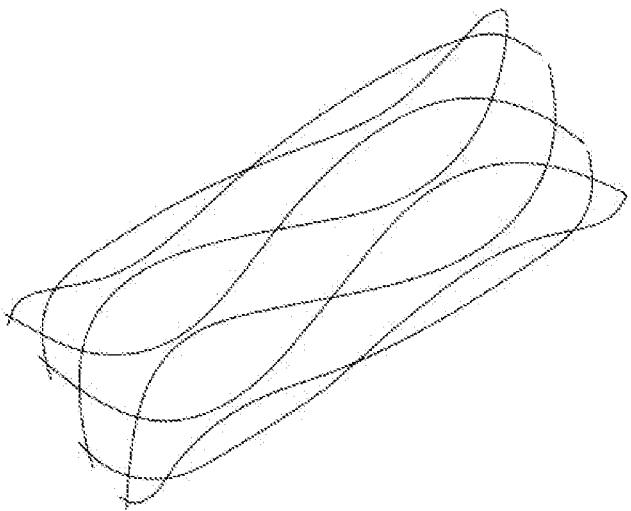
FIG. 6 is a structure schematic diagram of an adjustable stent made by a laser cutting process in accordance with an embodiment of the present disclosure.

In yet another embodiment, please referring to FIG. 6, the adjustable stent 21 is made by a laser cutting process.

In a more specific embodiment, the adjustable stent 21 is composed of nickel-titanium metal tubes having a diameter of 2 mm to 3 mm, which is cut into a designed net structure or stent structure by laser, and then is heat-treated by a setting die.

Some embodiments of the laser fiber bundle 10, the outer tube 30 and the overtube 40 are described below.

In an embodiment, the laser fiber bundle 10 consists of multiple uniformly arranged multimode fibers, and the tail ends of the multimode fibers are flush with the outer tube.

In a specific embodiment, a lens is fixedly connected to one end of the laser fiber bundle 10 that emits laser.

The advantage of providing the lens is that the laser emitted by the laser fiber bundle 10 can be gathered so as to ablate the lesion location better.

In a specific embodiment, the lens is made of a sapphire material.

The advantage of using the sapphire material is that the sapphire material has high hardness, good thermal characteristics, chemical corrosion resistance, high temperature resistance, and capability of satisfying visibility requirements under X-ray.

In an embodiment, the outer tube 30 is made of a polymer material, which includes, but is not limited to, poly(ether block amide) (Pebax), polyamide (PA), polytetrafluoroethylene (PTFE), or thermoplastic polyurethane elastomer rubber (TPU).

The advantage of using the polymer material is that the polymer material has low density, light weight under the same volume, high specific strength, good toughness and bending fatigue strength, and thus can well satisfy the use requirements in surgery. Moreover, due to the low friction coefficient, the PTFE material can provide better lubrication function to facilitate the laser ablation catheter to move in the vessel.

In another embodiment, both ends of the outer tube 30 are connected to both ends of the laser fiber bundle 10 by thermal splicing or glue bonding.

In still another embodiment, the surface of the outer tube 30 is covered with a medical hydrophilic coating. When the surface of the hydrophilic coating is exposed to water or moisture, water molecules can be captured and therefore the hydrophilic coating becomes lubricating upon wetting, thereby further increasing the lubricity of the outer tube 30.

In an embodiment, the overtube 40 is also made of a polymer material, which includes, but is not limited to, poly(ether block amide) (Pebax), polyamide (PA), polytetrafluoroethylene (PTFE), or thermoplastic polyurethane elastomer rubber (TPU).

In another embodiment, the surface of the overtube 40 is also covered with a hydrophilic coating to increase the lubricity.

The technical features of above embodiments may be arbitrarily combined, and all possible combinations of the technical features in the above embodiments are not described for simplicity of description. However, as long as the combinations of technical features do not contradict each other, the technical features should be considered to be within scope of description of the present disclosure.

The above embodiments represent only several embodiments of the present disclosure, and the description thereof is specific and detailed, but should not therefore be construed as limiting the scope of the present disclosure. It should be noted that for those of ordinary skill in the art, several variations and modifications can be made without departing from the concept of the present disclosure, all of which fall within the scope of protection of the present disclosure. Therefore, the scope of protection of the present disclosure shall be subject to the appended claims.

What is claimed is:

1. A laser ablation catheter, comprising: a laser fiber bundle, an adjustable head, an outer tube, an overtube, and a connector;

the outer tube wraps the laser fiber bundle, the adjustable head includes an adjustable stent, the adjustable stent is made of a shape memory material and is sleeved outside one end of the outer tube, the connector is connected to a second end of the outer tube, and the laser fiber bundle is able to be connected to a laser generator through the connector;

the overtube is sleeved outside the adjustable stent for compressing the adjustable stent;

one end of the adjustable stent is a movable end and the other end of the adjustable stent is a fixed end, wherein the movable end is slidingly connected to the outer tube; and when the overtube is withdrawn, the movable end provides conditions for deformation of the adjustable stent; such that the adjustable stent expands to abut against an inner wall of a target vessel and keeps the laser ablation catheter at a center of the target vessel;

wherein the fixed end is fixedly connected to the outer tube.

2. The laser ablation catheter according to claim 1, wherein the movable end is an end of the adjustable stent away from the connector, and the fixed end is an end of the adjustable stent close to the connector.

3. The laser ablation catheter according to claim 2, wherein a tail end of the outer tube is provided with a limiting stage for preventing the movable end from sliding out of the outer tube.

4. The laser ablation catheter according to claim 1, wherein the adjustable head further comprises an annular structure, and the annular structure is fixedly connected to both ends of the adjustable stent.

5. The laser ablation catheter according to claim 1, wherein the adjustable stent is made of nickel-titanium alloy.

6. The laser ablation catheter according to claim 5, wherein the adjustable stent is composed of nickel-titanium alloy wires manufactured by a weaving process.

7. The laser ablation catheter according to claim 5, wherein the adjustable stent is composed of nickel-titanium alloy sheets manufactured by a sheet metal process.

8. The laser ablation catheter according to claim 5, wherein the adjustable stent is made by a laser cutting process.

* * * * *